United States Patent
Park et al.

(10) Patent No.: US 11,434,480 B2
(45) Date of Patent: Sep. 6, 2022

(54) VIRAL RNA EXTRACTING COMPOSITION AND VIRAL RNA EXTRACTING METHOD

(71) Applicant: INDUSTRY FOUNDATION OF CHONNAM NATIONAL UNIVERSITY, Gwangju (KR)

(72) Inventors: Ki Beom Park, Gwangju (KR); Yong Hun Jo, Gwangju (KR); Yeon Soo Han, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 223 days.

(21) Appl. No.: 16/343,071

(22) PCT Filed: May 25, 2018

(86) PCT No.: PCT/KR2018/005978
§ 371 (c)(1),
(2) Date: Apr. 18, 2019

(87) PCT Pub. No.: WO2019/066188
PCT Pub. Date: Apr. 4, 2019

(65) Prior Publication Data
US 2020/0165598 A1 May 28, 2020

(30) Foreign Application Priority Data

Sep. 27, 2017 (KR) .................. 10-2017-0125547
Sep. 27, 2017 (KR) .................. 10-2017-0125548

(51) Int. Cl.
*C12N 15/10* (2006.01)
*C12Q 1/6806* (2018.01)

(52) U.S. Cl.
CPC ....... *C12N 15/1003* (2013.01); *C12Q 1/6806* (2013.01)

(58) Field of Classification Search
CPC .................. C12N 15/1003; C12Q 1/6806
USPC ..................................... 536/25.41
See application file for complete search history.

(56) References Cited

U.S. PATENT DOCUMENTS

| 2005/0123965 | A1* | 6/2005 | Yamashita | ........... C12N 15/101 435/6.16 |
| 2008/0003575 | A1 | 1/2008 | Michalik et al. | |
| 2014/0342938 | A1* | 11/2014 | Tischfield | ............. G16B 25/00 506/9 |
| 2016/0102304 | A1 | 4/2016 | Conrad | |

FOREIGN PATENT DOCUMENTS

GB         2538955 A   * 12/2016
KR   10-2002-0091627 A     12/2002

OTHER PUBLICATIONS

Mark A. Lever et al, "A modular method for the extraction of DNA and RNA, and the separation of DNA pools from diverse environmental sample types", Frontiers in Microbiology, 2015.
Catalog, "DNA & RNA Precipitation Solutions", Certificate of Analysis & Product Manual, 2014.
International Search Report from corresponding PCT Application No. PCT/KR2018/005978, dated Nov. 2, 2018.

* cited by examiner

*Primary Examiner* — Shaojia A Jiang
*Assistant Examiner* — Michael C Henry
(74) *Attorney, Agent, or Firm* — Harness, Dickey & Pierce, P.L.C.

(57) ABSTRACT

The present invention relates to a composition for viral RNA extraction and a viral RNA extraction method using the same, wherein various contaminants (e.g., fungi, bacteria, pollens, etc.) can be effectively removed from samples and thus the diagnosis of sample-derived viruses can be attained more sensitively, and more cheap reagents compared with existing compositions for RNA extraction are used and thus the scales of diagnosis tests of disease-mediated viruses and various monitoring programs can be further enlarged, thereby contributing to public health.

12 Claims, 3 Drawing Sheets
Specification includes a Sequence Listing.

VIRAL RNA EXTRACTING COMPOSITION AND VIRAL RNA EXTRACTING METHOD

CROSS-REFERENCE TO RELATED APPLICATIONS

This application is a national phase application of PCT Application No. PCT/KR2018/005978, filed on May 25, 2018, which claims priority to Korean Patent Application Nos. 10-2017-0125547 filed on Sep. 27, 2017 and 10-2017-0125548 filed on Sep. 27, 2017. The entire disclosures of the applications identified in this paragraph are incorporated herein by reference.

FIELD

The present invention relates to a composition for viral RNA extraction and a viral RNA extraction method using the same.

BACKGROUND

In conventional RNA solid-phase extraction techniques, RNA is extracted using a guanidine salt as a chaotropic salt. According to existing research papers, guanidine salt, which is a strong chaotropic salt, denatures protein membranes enclosing cells or viruses to elute RNA from tissues or cells. The eluted RNA is allowed to react with a silica membrane. In high-salt conditions, positively (+) charged salt bridges are formed at negative (−) charges of the silica membrane, and negatively (−) charged sites of nucleic acids bind to the bridges. Thereafter, nucleic acids, such as RNA, can be extracted from the silica membrane by using low-salt water or a particular buffer.

Such an RNA extraction method using a chaotropic salt is convenient for experimental procedures and causes low toxicity, and even beginners can extract high-quality nucleic acids when they faithfully follow manuals for the method. However, the high price of kits causes economic problems when RNA is extracted from a large quantity of samples.

Meanwhile, a liquid-phase separation RNA extraction technique using Trizol employs phenol, chloroform, or guanidine thiocyanate. Each component serves to destroy protein membranes of cells or biological tissues to elute intracellular DNA or RNA. Such a liquid-phase separation RNA extraction technique using Trizol is different from a method using a silica membrane in that RNA is extracted by separation of layers through centrifugation without using a solid membrane.

In the liquid-phase separation RNA extraction technique using Trizol, on the basis of the facts that proteins are lysed in phenol, phenol is dissolved in chloroform, and DNA is more easily isolated in acidic conditions than RNA, the separation of a protein layer (phenol layer >1.49 g/cm$^3$), a DNA layer (1.03> middle layer >1.49 g/cm$^3$), and an RNA layer (1 g> water layer >1.03 g/cm$^3$) occurs through centrifugation, and a supernatant is subjected to precipitation using isopropanol, thereby extracting pure RNA. The liquid-phase separation RNA extraction technique is used for the purpose of treating a large amount or number of samples due to a low cost thereof. However, skilled experimental techniques are required and volatile toxic substances, such as phenol and chloroform, are used, and thus the lack of establishment of appropriate facilities for preventing the exposure to harmful substances may cause harm to the health of experimenters.

SUMMARY

Technical Problem

The present inventors endeavored to extract RNA from a sample to diagnose whether or not the sample has viruses. As a result, the present inventors developed a composition capable of efficiently isolating virus-derived RNA while excluding the use of harmful substances to the human body and removing contaminants (e. g., proteins, RNA, DNA, carbohydrates, etc.) originated from fungi, pollens, and the like, and a viral RNA extraction method using the composition, and thus completed the present invention.

Therefore, an aspect of the present invention is to provide a composition for viral RNA extraction.

Another aspect of the present invention is to provide a viral RNA extraction method.

Technical Solution

In accordance with an aspect of the present invention, there is provided a composition for viral RNA extraction, the composition including:

(a) a homogenization solution containing, relative to a total amount thereof, 1-30 mM ethylenediaminetetraacetic acid (EDTA) and 0.1-2% (v/v) sodium chloride (NaCl);

(b) a lysis buffer containing, relative to a total amount thereof, 0.1-1.5 M NaCl and 0.1-10% (v/v) sodium dodecyl sulfate (SDS); and (c) a primary wash buffer containing, relative to a total amount thereof, 1-5 M sodium acetate.

The viral RNA extracted through the composition for viral RNA extraction can be used to diagnose whether or not a sample has viruses.

The composition for viral RNA extraction of the present invention may be used to extract viral RNA from a sample.

The sample may be an animal or a liquid.

The animal may be an arthropod, for example, an insect, an arachnid, or a myriapod, but is not limited thereto.

The insect may be a bee, a mosquito, a fly, a butterfly, a moth, an ant, a dragonfly, a cockroach, a mantis, a stick insect, a locust, a cicada, or a beetle, but is not limited thereto.

The arachnid may be a spider, a scorpion, or a mite, but is not limited thereto.

The myriapod may be a centipede, a millipede, or a house centipede, but is not limited thereto.

In a case where the sample is an animal, the sample may be an individual being, a tissue, an organ, or cells of the animal, but is not limited thereto.

The liquid may be seawater, tap water, bottled water, or water in a fish farm, but is not limited thereto.

According to an embodiment of the present invention, the animal may be collected outdoors, and for example, may be an insect collected outdoors, but is not limited thereto.

The composition for viral RNA extraction of the present invention may contain a homogenization solution.

The term "homogenization" refers to the formation of a homogeneous solution from the disruption of a sample, and means that, for example, a sample collected in order to extract viral RNA is mixed with a homogenization solution and the mixture is homogenized by disruption with a homogenizer.

The homogenization solution may contain ethylenediaminetetraacetic acid (EDTA) and sodium chloride (NaCl).

The EDTA may be contained at a concentration of, relative to a total amount of the homogenization solution, 1.0-30 mM, 1.0-28 mM, 1.0-25 mM, 1.0-22 mM, 3.0-30 mM, 3.0-28 mM, 3.0-25 mM, 3.0-22 mM, 5.0-30 mM, 5.0-28 mM, 5.0-25 mM, 5.0-22 mM, 8.0-30 mM, 8.0-28 mM, 8.0-25 mM, 8.0-22 mM, 10-30 mM, 10-28 mM, 10-25 mM, 10-22 mM, 12-30 mM, 12-28 mM, 12-25 mM, 12-22 mM, 15-30 mM, 15-28 mM, 15-25 mM, 15-22 mM, 18-30 mM, 18-28 mM, 18-25 mM, 18-22 mM, or 19-21 mM, and for example, may be contained at a concentration of 20 mM.

The NaCl may be contained at a concentration of, relative to the homogenization solution, 0.1-2.0% (v/v), 0.1-1.8% (v/v), 0.1-1.5% (v/v), 0.1-1.2% (v/v), 0.1-1.0% (v/v), 0.3-2.0% (v/v), 0.1-1.8% (v/v), 0.3-1.5% (v/v), 0.3-1.2% (v/v), 0.3-1.0% (v/v), 0.5-2.0% (v/v), 0.5-1.8% (v/v), 0.5-1.5% (v/v), 0.5-1.2% (v/v), 0.5-1.0% (v/v), 0.8-2.0% (v/v), 0.8-1.8% (v/v), 0.8-1.5% (v/v), 0.8-1.2% (v/v), 0.8-1.0% (v/v), or 0.8-0.9% (v/v), and for example, may be contained at a concentration of 0.9% (v/v).

The composition for viral RNA extraction of the present invention may contain a lysis and binding buffer.

The lysis and binding buffer may contain sodium dodecyl sulfate (SDS) and sodium chloride (NaCl).

In the lysis and binding buffer, SDS may be contained at a concentration of 0.1-10.0% (v/v), 0.1-9.0% (v/v), 0.1-8.0% (v/v), 0.1-7.0% (v/v), 0.5-10.0% (v/v), 0.5-9.0% (v/v), 0.5-8.0% (v/v), 0.5-7.0% (v/v), 1.0-10.0% (v/v), 1.0-9.0% (v/v), 1.0-8.0% (v/v), 1.0-7.0% (v/v), 2.0-10.0% (v/v), 2.0-9.0% (v/v), 2.0-8.0% (v/v), 2.0-7.0% (v/v), 3.0-10.0% (v/v), 3.0-9.0% (v/v), 3.0-8.0% (v/v), 3.0-7.0% (v/v), 4.0-10.0% (v/v), 4.0-9.0% (v/v), 4.0-8.0% (v/v), 4.0-7.0% (v/v), 5.0-10.0% (v/v), 5.0-9.0% (v/v), 5.0-8.0% (v/v), or 5.0-7.0% (v/v), and for example, may be contained at a concentration of 6.0% (v/v).

In the lysis and binding buffer, NaCl may be contained at a concentration of 0.5-1.0 M, 0.5-0.9 M, 0.5-0.8 M, 0.5-0.75 M, 0.6-1.0 M, 0.6-0.9 M, 0.6-0.8 M, 0.6-0.75 M, 0.7-1.0 M, 0.7-0.9 M, 0.7-0.8 M, or 0.7-0.75 M, and for example, may be contained at a concentration of 0.75 M.

When NaCl is contained at 1 M or more in the lysis and binding buffer, SDS is precipitated as an insoluble form, and when NaCl is contained at less than 0.5 M, insect cells in the homogenized solution cannot be effectively lysed due to low osmotic pressure.

The composition for viral RNA extraction of the present invention may contain a primary wash buffer containing sodium acetate.

The primary wash buffer may contain sodium acetate at a concentration of 1-5 M, 1-4 M, 1-3 M, 2-5 M, 2-4 M, 2-3 M, 3-5 M, or 3-4 M, and for example, may be contained at a concentration of 3 M.

The pH of the primary wash buffer may be 4.0-6.0, 4.0-5.5, 4.5-6.0, 4.5-5.5, 5.0-5.5, or 5.0-6.0, and for example, may be 5.5.

In general, 3 M of sodium acetate is used when RNA or DNA is washed. It is known that DNA favorably binds to silica membranes in neutral or basic pH, but the binding ability of DNA is reduced in acidic pH. On the contrary, the binding ability of RNA increases in an acidic state, and the stability of RNA increases in a weak acid state rather than a basic state, resulting in a reduction in RNA degradation rate.

In accordance with an aspect of the present invention, there is provided a viral RNA extraction method, the method including:

(a) a homogenizing step of homogenizing a sample;

(b) a first centrifuging step of centrifuging the homogenized solution;

(c) a first mixing step of mixing a lysis buffer with a first centrifugation supernatant;

(d) a second centrifuging step of centrifuging a lysis buffer mixture;

(e) a second mixing step of mixing isopropanol with a second centrifugation supernatant;

(f) a step of passing an isopropanol mixture through a silica membrane column;

(g) a washing step of passing a wash buffer through the silica membrane column to wash the silica membrane column; and (h) an eluting step of eluting RNA from the silica membrane column.

The present invention is directed to a viral RNA extraction method, and the RNA extracted through the method can be used to diagnose whether or not a sample has viruses.

Existing viral RNA extraction kits employ high-price reagents, such as guanidine thiocyanate, sodium iodide, and guanidine hydrochloride. Therefore, experiments in which large populations of insects are subjected to RNA extraction using an existing viral RNA extraction kit and diagnosis of the presence or absence of viruses cause a great economic burden. In addition, experimental materials contained in the kit, such as a strong chaotropic salt, for example, a guanidine salt, or phenol and chloroform contained in Trizol, are harmful to the human body, and thus when experimenters are exposed to such experimental materials for a long period of time, the experimental materials do harm to the health of the experimenters.

Existing viral RNA extraction kits and extraction methods are based on the extraction of viruses from human body-derived samples or cell cultures. Therefore, a lot of contaminants are not present in an initial sample per se. However, insects are often collected outdoors, and in such a case, various contaminants (e. g., fungi, bacteria, pollens, etc.) are present.

Existing viral RNA extraction kits use a strong chaotropic salt, and thus extract not only insect RNA and virus-derived RNA, but also all species of RNA of fungi, bacteria, plant materials (e. g., pollens, etc.), which are contaminants. The RNA derived from various contaminants resultantly acts as an inhibitor during polymerase chain reaction (PCR) performed in diagnosis tests, thereby lowering sensitivity in diagnosis of the presence or absence of viruses.

The present invention is to solve problems occurring when viral RNA is extracted from a sample by using a chaotropic salt. Specifically, RNA is extracted using a lysis and binding buffer having low solubility of contaminants, such as fungi and pollens, and high solubility of viruses.

In addition, the sensitivity in diagnostic test at the time of diagnosis of whether or not a sample has viruses is improved by removing contaminants (for example, small RNA, proteins, DNA, hydrocarbons, or the like) as much as possible through centrifugation, and the cost of RNA extraction can be remarkably lowered by using cheaper chemicals compared with existing viral RNA extraction kits.

Currently, diagnostic tests of disease-medicated viruses and various monitoring programs are restricted for economic reasons. Out of these, the extraction of RNA from mosquitoes is the most costly, and it is expected that if such a procedure can be carried out at a lower cost through the present invention, the scale of monitoring programs can be further enlarged, thereby contributing to public health.

The viral RNA extraction method of the present invention will be described in detail by steps.

(a) Homogenization of Sample

In order to extract viral RNA from a sample, the sample is first homogenized.

The sample may be an animal or a liquid.

The animal may be an arthropod, for example, an insect, an arachnid, or a myriapod, but is not limited thereto.

The insect may include a bee, a mosquito, a fly, a butterfly, a moth, an ant, a dragonfly, a cockroach, a mantis, a stick insect, a locust, a cicada, and a beetle, but is not limited thereto.

The arachnid may include a spider and a scorpion, but is not limited thereto.

The myriapod may include a centipede, a millipede, and a house centipede, but is not limited thereto.

In a case where the sample is an animal, the sample may be an individual being, a tissue, an organ, or cells of the animal, but is not limited thereto.

The liquid may be seawater, tap water, bottled water, or water in a fish farm, but is not limited thereto.

According to an embodiment of the present invention, the animal may be collected outdoors, and for example, may be an insect collected outdoors, but is not limited thereto.

The term "homogenization" refers to the formation of a homogeneous solution from the disruption of a sample. For example, a sample collected in order to extract of viral RNA is mixed with a homogenization solution and the mixture is homogenized by disruption with a homogenizer.

The homogenization may be carried out by adding, to a sample, a homogenization solution containing, relative to a total amount thereof, 1-30 mM ethylenediaminetetraacetic acid (EDTA) and 0.1-2.0% (v/v) NaCl.

The EDTA may be contained at a concentration of, relative a total amount of the homogenization solution, 1.0-30 mM, 1.0-28 mM, 1.0-25 mM, 1.0-22 mM, 3.0-30 mM, 3.0-28 mM, 3.0-25 mM, 3.0-22 mM, 5.0-30 mM, 5.0-28 mM, 5.0-25 mM, 5.0-22 mM, 8.0-30 mM, 8.0-28 mM, 8.0-25 mM, 8.0-22 mM, 10-30 mM, 10-28 mM, 10-25 mM, 10-22 mM, 12-30 mM, 12-28 mM, 12-25 mM, 12-22 mM, 15-30 mM, 15-28 mM, 15-25 mM, 15-22 mM, 18-30 mM, 18-28 mM, 18-25 mM, 18-22 mM, or 19-21 mM, and for example may be contained at a concentration of 20 mM.

The NaCl may be contained at a concentration of, relative to the homogenization solution, 0.1-2.0% (v/v), 0.1-1.8% (v/v), 0.1-1.5% (v/v), 0.1-1.2% (v/v), 0.1-1.0% (v/v), 0.3-2.0% (v/v), 0.1-1.8% (v/v), 0.3-1.5% (v/v), 0.3-1.2% (v/v), 0.3-1.0% (v/v), 0.5-2.0% (v/v), 0.5-1.8% (v/v), 0.5-1.5% (v/v), 0.5-1.2% (v/v), 0.5-1.0% (v/v), 0.8-2.0% (v/v), 0.8-1.8% (v/v), 0.8-1.5% (v/v), 0.8-1.2% (v/v), 0.8-1.0% (v/v), or 0.8-0.9% (v/v), and for example, may be contained at a concentration of 0.9% (v/v).

(b) First Centrifugation

The homogenized solution is subjected to first centrifugation to obtain a supernatant containing viral RNA.

(c) Mixing Lysis and Binding Buffer with First Centrifugation Supernatant

A lysis and binding buffer is mixed with a supernatant obtained from the first centrifugation.

The lysis and binding buffer may contain sodium dodecyl sulfate (SDS) and sodium chloride (NaCl).

In the lysis and binding buffer, SDS may be contained at a concentration of 0.1-10.0% (v/v), 0.1-9.0% (v/v), 0.1-8.0% (v/v), 0.1-7.0% (v/v), 0.5-10.0% (v/v), 0.5-9.0% (v/v), 0.5-8.0% (v/v), 0.5-7.0% (v/v), 1.0-10.0% (v/v), 1.0-9.0% (v/v), 1.0-8.0% (v/v), 1.0-7.0% (v/v), 2.0-10.0% (v/v), 2.0-9.0% (v/v), 2.0-8.0% (v/v), 2.0-7.0% (v/v), 3.0-10.0% (v/v), 3.0-9.0% (v/v), 3.0-8.0% (v/v), 3.0-7.0% (v/v), 4.0-10.0% (v/v), 4.0-9.0% (v/v), 4.0-8.0% (v/v), 4.0-7.0% (v/v), 5.0-10.0% (v/v), 5.0-9.0% (v/v), 5.0-8.0% (v/v), or 5.0-7.0% (v/v), and for example, may be contained at a concentration of 6.0% (v/v).

Previous studies have shown that when the SDS concentration in a working solution is finally about 2.0% (v/v), such a concentration is sufficient to extract RNA from a sample (Appl Environ Microbiol. 2011 June; 77(12): 3975-3981). Tests confirmed that there was no problem in RNA extraction even when SDS was used at concentrations of 1.0% (v/v) and 1.5% (v/v), but the following problems occurred.

In a precipitation reaction using SDS and NaCl to remove DNA and proteins, a low concentration of SDS decreased the size of precipitated pellets, making it difficult to separate a supernatant, and a higher concentration of SDS than the above range caused a lot of bubbles, making a melting procedure immediately before an experiment difficult, so that the experiment is not easy to carry out. Therefore, the concentration of SDS was determined to be 6.0% (v/v) in a lysis and binding buffer (LnB).

Furthermore, the concentration of SDS as a main ingredient in RNAse ZAP, which removes RNAase as an RNA degrading enzyme, was estimated to be about 1.0-5.0% (v/v), and on the basis of the fact, it was determined that the final concentration of SDS should be 1.0% (v/v) or more to effectively deactivate RNAse, and the SDS concentration of the lysis and binding buffer (LnB) was determined to be 6.0% (v/v) so that the concentration of SDS was about 2.0% (v/v) when a solution containing RNA was finally passed through a column.

In the lysis and binding buffer, NaCl may be contained at a concentration of 0.5-1.0 M, 0.5-0.9 M, 0.5-0.8 M, 0.5-0.75 M, 0.6-1.0 M, 0.6-0.9 M, 0.6-0.8 M, 0.6-0.75 M, 0.7-1.0 M, 0.7-0.9 M, 0.7-0.8 M, or 0.7-0.75 M, and for example, may be contained at a concentration of 0.75 M.

When NaCl is contained at 1.0 M or more in the lysis and binding buffer, SDS is precipitated as an insoluble form, and when NaCl is contained at less than 0.5 M, insect cells in a homogenized solution cannot be effectively lysed due to low osmotic pressure.

The lysis and binding buffer may be mixed at 0.6-1.3 times (v/v), 0.6-1.2 times (v/v), 0.6-1.1 times (v/v), 0.6-1.0 times (v/v), 0.7-1.3 times (v/v), 0.7-1.2 times (v/v), 0.7-1.1 times (v/v), 0.7-1.0 times (v/v), 0.8-1.3 times (v/v), 0.8-1.2 times (v/v), 0.8-1.1 times (v/v), 0.8-1.0 times (v/v), 0.9-1.3 times (v/v), 0.9-1.2 times (v/v), 0.9-1.1 times (v/v), or 0.9-1.0 times (v/v) relative to a supernatant obtained by performing first centrifugation on the homogenized solution, which was obtained by adding the homogenization solution to a sample, followed by homogenization, and for example, may be mixed at 1.0 time (v/v).

The maximum volume of a column used to bind nucleic acids is generally 700 µl, and about 600 µl of a sample should be loaded into the column to reduce the contamination of column membranes by waste passing through the column. When 100 µl of the first centrifugation supernatant is used, the addition of 100 µl of the lysis and binding buffer and 100 µl of 5 M NaCl aqueous solution results in 300 µl, the total volume of the mixture.

Since the final concentration of isopropanol used to bind nucleic acids to membranes should be 50% (v/v) (DNA or RNA precipitation being generally carried out at a final concentration of 50% (v/v), 300 µl of isopropanol is used when the total volume of a mixture of the centrifugation supernatant, lysis and binding buffer, and 5 M NaCl aqueous solution is 300 µl. Therefore, the volume of the mixture loaded into a column is eventually 600 µl. Therefore, it is determined that the lysis and binding buffer is mixed at 1.0 time (v/v) relative to the first centrifugation supernatant.

According to an embodiment of the present invention, the lysis and binding buffer may be mixed at the same amount (v/v) as a supernatant, which is obtained by performing first centrifugation on the homogenized solution obtained by adding the homogenization solution to the sample, followed by homogenization.

According to an embodiment of the present invention, NaCl may be added to a mixture obtained by mixing the supernatant obtained from the first centrifugation and the lysis and binding buffer.

The added NaCl may be in a state of NaCl aqueous solution.

The NaCl aqueous solution may have a concentration of 1-10 M, 1-8 M, 1-7 M, 1-6 M, 2-10 M, 2-8 M, 2-7 M, 2-6 M, 3-10 M, 3-8 M, 3-7 M, 3-6 M, 4-10 M, 4-8 M, 4-7 M, or 4-6 M, and for example may be a 5 M NaCl aqueous solution.

The NaCl aqueous solution may be mixed at 0.6-1.3 times (v/v), 0.6-1.2 times (v/v), 0.6-1.1 times (v/v), 0.6-1.0 times (v/v), 0.7-1.3 times (v/v), 0.7-1.2 times (v/v), 0.7-1.1 times (v/v), 0.7-1.0 times (v/v), 0.8-1.3 times (v/v), 0.8-1.2 times (v/v), 0.8-1.1 times (v/v), 0.8-1.0 times (v/v), 0.9-1.3 times (v/v), 0.9-1.2 times (v/v), 0.9-1.1 times (v/v), or 0.9-1.0 times (v/v), relative to a mixture obtained by mixing the aqueous solution obtained from the first centrifugation and the lysis and binding buffer, and for example, may be mixed at the same amount (v/v).

The NaCl aqueous solution, which is added to the mixture obtained by mixing the supernatant obtained from the first centrifugation and the lysis and binding buffer, may be mixed at the same amount (v/v) with the supernatant.

According to an embodiment of the present invention, 100 µl of the lysis and binding buffer may be mixed with 100 µl of the supernatant obtained from the first centrifugation, and then 100 µl of 5 M NaCl aqueous solution may be mixed therewith.

(d) Centrifugation of Lysis and Binding Buffer Mixture (Second Centrifugation)

The mixture obtained by mixing the supernatant obtained from the first centrifugation and the lysis and binding buffer is subjected to second centrifugation.

(e) Mixing of Isopropanol with Centrifugation Supernatant

A supernatant obtained from the second centrifugation is transferred into a new tube, and isopropanol is mixed therewith.

The isopropanol may be mixed at the amount of 0.6-1.3 times (v/v), 0.6-1.2 times (v/v), 0.6-1.1 times (v/v), 0.6-1.0 times (v/v), 0.7-1.3 times (v/v), 0.7-1.2 times (v/v), 0.7-1.1 times (v/v), 0.7-1.0 times (v/v), 0.8-1.3 times (v/v), 0.8-1.2 times (v/v), 0.8-1.1 times (v/v), 0.8-1.0 times (v/v), 0.9-1.3 times (v/v), 0.9-1.2 times (v/v), 0.9-1.1 times (v/v), or 0.9-1.0 times (v/v), relative to the supernatant obtained from the second centrifugation, and for example, may be mixed at the same amount as the supernatant.

According to an embodiment of the present invention, the isopropanol, which is added with the supernatant obtained from the second centrifugation, may be mixed at the same amount (v/v) as the supernatant obtained from the second centrifugation.

(f) Passing of Isopropanol Mixture Through Column

The mixture obtained by mixing the supernatant obtained from the second centrifugation and isopropanol is passed through a silica membrane column.

The silica membrane column is not particularly limited as long as it is a column of a silica material.

(g) Column Washing

The silica membrane column is washed by adding a wash buffer thereto, followed by centrifugation.

The wash buffer may contain, relative to a total amount thereof, 1-5 M sodium acetate.

The sodium acetate in the wash buffer may be contained at a concentration of, relative to a total amount of the wash buffer, 1-5 M, 1-4 M, 1-3 M, 2-5 M, 2-4 M, 2-3 M, 3-5 M, or 3-4 M, and for example, may be contained at a concentration of 3 M.

The pH of the primary wash buffer may be 4.0-6.0, 4.0-5.5, 4.5-6.0, 4.5-5.5, 5.0-5.5, or 5.0-6.0, and for example, may be 5.5.

According to an embodiment of the present invention, the silica membrane column washed with the primary wash buffer may be further washed with a secondary wash buffer.

The secondary wash buffer may be a 70-90% (v/v) ethanol aqueous solution, and for example, may be 80% (v/v) ethanol aqueous solution.

The silica membrane column may be washed with the ethanol aqueous solution to remove the previously used buffer ingredients.

(h) RNA Elution

RNA is eluted from the washed silica membrane column.

The RNA elution may be performed by introducing an elution buffer into the silica membrane column, followed by centrifugation.

The elution buffer may be water free from RNAase.

Advantageous Effects

The present invention is directed to a composition for viral RNA extraction and a viral RNA extraction method using the same, wherein various contaminants (e. g., fungi, bacteria, pollens, etc.) can be effectively removed from samples and thus the diagnosis of sample-derived viruses can be attained more sensitively, and more cheap reagents compared with existing compositions for RNA extraction are used and thus the scales of diagnosis tests of disease-mediated viruses and various monitoring programs can be further enlarged, thereby contributing to public health.

BEST MODE FOR CARRYING OUT THE INVENTION

Figure 1:
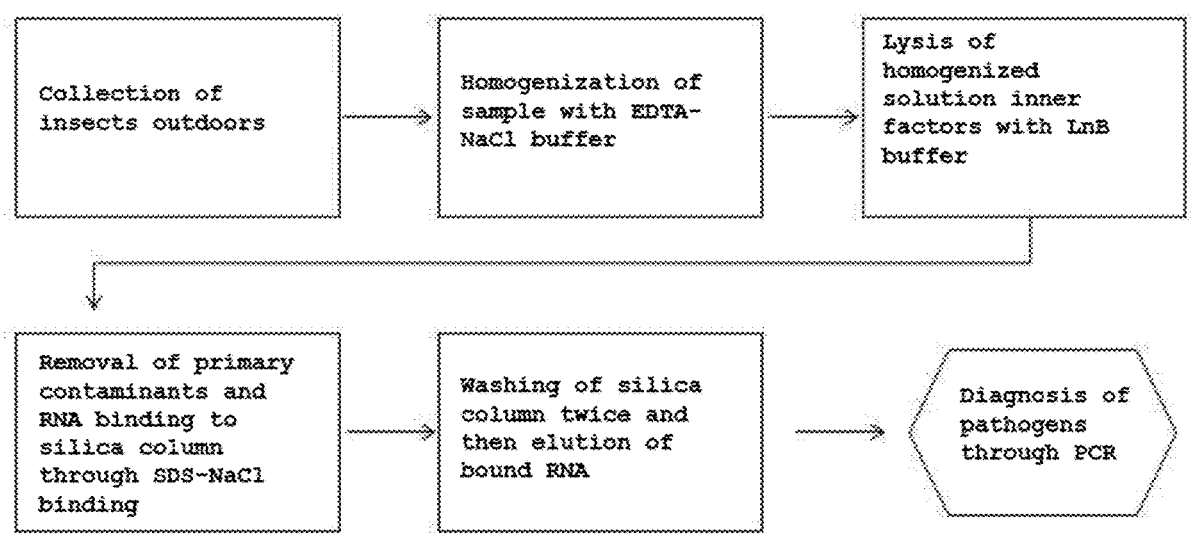
FIG. 1 is a schematic diagram of a method for extracting viral RNA from an insect sample according to an example of the present invention.

A composition for viral RNA extraction, the composition including:

(a) a homogenization solution containing, relative to a total amount thereof, 1-30 mM ethylenediaminetetraacetic acid (EDTA) and 0.1-2% (v/v) sodium chloride (NaCl);

(b) a lysis buffer containing, relative to a total amount thereof, 0.1-1.5 M NaCl and 0.1-10% (v/v) sodium dodecyl sulfate (SDS); and (c) a primary wash buffer containing, relative to a total amount thereof, 1-5 M sodium acetate.

DETAILED DESCRIPTION

Hereinafter, the present invention will be described in more detail with reference to the following examples. However, these examples are given for illustrating the present invention, and the scope of the present invention is not limited thereto.

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

1. EXAMPLE

1-1. Homogenizing Step

A homogenized solution was obtained by adding 1 ml of 20 mM EDTA-0.9% NaCl solution per 300 mg of insects, followed by homogenization.

1-2. First Centrifuging Step

A supernatant was obtained by subjecting the homogenized solution to first centrifugation in the condition of 5,000 g/10 min.

1-3. First Mixing Step

100 μl of the supernatant from the homogenized solution subjected to the first centrifugation was heated to 70° C., and 100 μl of the lysis and binding buffer (LnB) in table 1 was added, followed by stirring, and then 100 μl of 5 M NaCl aqueous solution was added, followed by vortexing.

TABLE 1

| Ingredient | Volumn | Final concentration |
| --- | --- | --- |
| 20% SDS solution | 15 ml | 6% |
| 5 M NaCl | 7.5 ml | 0.75 M |
| Distilled water | 27.5 ml | — |

1-4. Second Centrifuging Step

Then, the lysis and binding buffer mixture was subjected to second centrifugation in conditions of 14,000 rpm and 4° C. for 5 minutes. Proteins and DNA were removed through this step. In this step, contaminants originated from the outside were removed.

The contaminants originated from the outside mean non-target organisms outside the insect bodies.

When SDS at a concentration of 0.5 to 6.0% (v/v) and aqueous NaCl solution at a concentration of 0.4 M or more are mixed, SDS is separated and precipitated. In this process, proteins and DNA that bind to SDS co-precipitate and are mostly removed from the supernatant. Therefore, it is possible to prevent the column clogging phenomenon when the unsolvable substances precipitated together with the SDS and NaCl precipitate are mixed together when the supernatant is transferred.

1-5. Second Mixing Step

A supernatant obtained from the second centrifugation was transferred into a new tube, and isopropanol was added and mixed at the same amount.

1-6. Column Passage Step

The mixture of the second centrifugation supernatant and isopropanol was added to a silica membrane column (Bioneer: KA-0133, DNA binding column tube for K-3034, Elpis: EBD-1021, Spin Column (mini), Zymoresearch: R2050, Spin column (miniprep), Qiagen: column in QIAamp Viral RNA mini kit), followed by centrifugation for 1 minute, thereby removing a liquid passing through the column. In this procedure, care should be taken that the liquid passing through the column does not touch the column.

1-7. Primary Washing Step

A primary wash buffer having a composition shown in Table 2 was added at a volume of 600 μl to the silica membrane column, followed by centrifugation for 1 minute, and a liquid passing through the column was removed. The pigments, proteins, DNA, hydrocarbons, and the like of insects were removed through this procedure. Here, care should be taken that the liquid passing through the column does not touch the column

TABLE 2

| Ingredient | Volume | Final concentration | pH |
| --- | --- | --- | --- |
| Sodium acetate | 12.3 g | 3M | — |
| Distilled water | Being added such that wash buffer had a final volumne of 50 ml | — | 5.5 |

1-8. Secondary Washing Step

A secondary wash buffer having a composition shown in Table 3 was added at a volume of 600 μl, followed by centrifugation for 2 minutes, and a liquid passing through the column was removed. Through this step, the ingredients of the lysis and binding buffer and the primary wash buffer used in the experiment were removed. In this procedure, care should be taken that the liquid passing through the column does not touch the column

TABLE 3

| Ingredient | Volume | Final concentration |
| --- | --- | --- |
| 99% Ethanol | 40 ml | 80% |
| Distilled water | 10 ml | — |

1-9. Elusion Step

RNA was eluted by adding 10-50 μl of distilled water to the column, and subjected to third centrifugation, thereby obtaining RNA.

2. Control Group

In order to assess efficiency of the composition for viral RNA extraction of the present invention, the QIAamp Viral RNA mini kit by Qiagen was used as a control group to extract RNA from the same insect sample.

Test Example 1. Absorbance Measurement

The absorbance of honeybee RNA extracted using the composition for viral RNA extraction of the present invention was measured at wavelengths of 230 nm, 260 nm, 280 nm, and 320 nm, and the absorbance ratios of 260 nm/230 nm and 260 nm/280 nm were calculated. The results are shown in Table 4.

In order to measure purity of nucleic acids, especially, purity of RNA, both the absorbance at 260 nm and the absorbance at 280 nm were measured to calculate the absorbance ratio of 260/280. The reason for the measurement at 280 nm is that amino acids, such as tyrosine and tryptophan, which have an aromatic ring structure in proteins, exhibit maximum absorption at 280 nm. From the calculation of such a ratio, it can be seen how much proteins the separated RNA solution contains.

As for RNA, the absorbance ratio of 260/230 was also calculated in addition to the ratio of 260/280. Since solvents such as phenol, salts, and proteins show high absorbance at 230 nm, it can be seen whether or not a sample was contaminated with such substances.

The 260/280 value of the purely isolated RNA was 1.9-2.2, and the value of 260/230 thereof was 1.8 or greater. That is a value of 260/230 of 1.8 or smaller indicates that a sample was contaminated with phenol, thiocyanate, guanidine, alcohol, and other organic solvents among the reagents used during the extraction of isolated RNA.

TABLE 4

| Sample Read# | Location | 260 | 280 | 230 | 260/280 | 260/230 | ng/μL |
|---|---|---|---|---|---|---|---|
| 1 | F2 | 0.149 | 0.068 | 0.061 | 2.181 | 2.441 | 118.932 |
| 1 | F3 | 0.15 | 0.069 | 0.062 | 2.18 | 2.435 | 120.127 |
| 1 | G2 | 0.143 | 0.066 | 0.059 | 2.182 | 2.434 | 114.532 |
| 1 | G3 | 0.133 | 0.061 | 0.055 | 2.187 | 2.432 | 106.128 |

It can be confirmed from Table 4 that the ratio of 260/280 of RNA extracted through the present invention had an average of 2.18 and the ratio of 260/230 thereof had an average of 2.43, indicating high purity.

Test Example 2. Diagnosis of Honeybee Viruses

As for RNA extracted by using the composition for viral RNA extraction of the present invention and RNA (control group) extracted using the QIAamp Viral RNA mini kit by Qiagen for 6 honeybee samples, viral RNA was detected using primer pairs specific to 7 species of honeybee viruses (CBPV: Chronic bee paralysis virus, BQCV: Black queen cell virus, ABPV: Acute bee paralysis virus, KBV: Kashmir bee virus, SBV: Sacbrood virus, DWV: Deformed wing virus, and IAPV: Israeli acute paralysis virus).

TABLE 5

| Virus | Name | SEQ ID NO | Pirmier sequence (5'-3') |
|---|---|---|---|
| CBPV | mpBEE-CBPV-F-774 | 1 | AACCTGCCTCAACACAGGCAAC |
|  | mpBEE-CBPV-R-774 | 2 | ACATCTCTTCTTCGGTGTCAGCC |
| BQCV | mpBEE-BQCV-F-536 | 3 | CTTTATCGAGGAGGAGTTCGAGT |
|  | mpBEE-BQCV-R-536 | 4 | GCAATAGATAAAGTGAGCCCTCC |

TABLE 5-continued

| Virus | Name | SEQ ID NO | Pirmier sequence (5'-3') |
|---|---|---|---|
| ABPV | mpBEE-ABPV-F-460 | 5 | GGTGCCCTATTTAGGGTGAGGA |
|  | mpBEE-ABPV-R-460 | 6 | ACTACAGAAGGCAATGTCCAAGA |
| KBV | mpBEE-KBV-F-415 | 7 | GATGAACGTCGACCTATTGA |
|  | mpBEE-KBV-R-415 | 8 | TGTGGGTGGCTATGAGTCA |
| SBV | mpBEE-SBV-F-342 | 9 | CGTAATTGCGGAGTGGAAAGATT |
|  | mpBEE-SBV-R-342 | 10 | AGATTCCTTCGAGGGTACCTCATC |
| DWV | mpBEE-DWV-F-269 | 11 | TGGTCAATTACAAGCTACTTGG |
|  | mpBEE-DWV-R-269 | 12 | TAGTTGGACCAGTAGCACTCAT |
| IAPV | mpBEE-IAPV-F-158 | 13 | GGTGCCCTATTTAGGGTGAGGA |
|  | mpBEE-IAPV-R-158 | 14 | GGGAGTATTGCTTTCTTGTTGTG |

TABLE 6

| PreDenature) | 94° C. | 2 min |
|---|---|---|
| Denature | 94° C. | 30 sec |
| Primer Annealing | 56° C. | 30 sec |
| Extension | 72° C. | 55 sec |
| 30 Cycles | | |
| Final Extension | 72° C. | 10 min |

* 1 step PCR: cDNA synthesis 50° C., 30 min,
* Enzyme activation: 95° C., 15 min
* DiaStar ™ 2X OneStep Multiplex qRT-PCR Smart mix (for Probe)

TABLE 7

|  | Sample 1 | Sample 2 | Sample 3 | Sample 4 | Sample 5 | Sample 6 |
|---|---|---|---|---|---|---|
| CBPV | W | W | V |  |  | W |
| BQCV | V | V | W | W | W | V |
| ABPV |  |  |  |  |  |  |
| KBV |  |  |  |  |  |  |
| SBV |  |  |  |  | V |  |
| DWV |  |  |  |  |  |  |
| IAPV |  |  |  |  |  |  |

Figure 2:
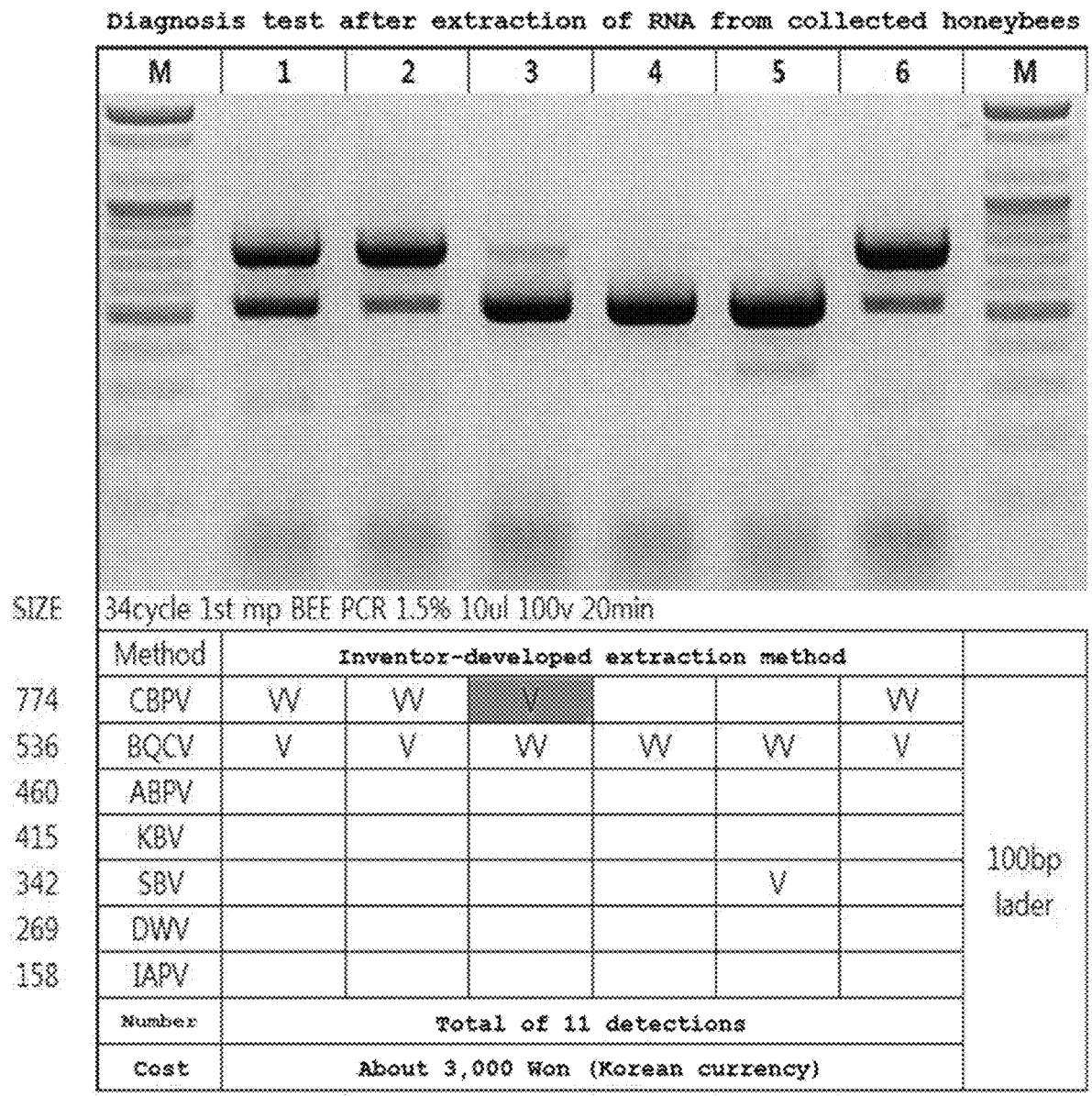
FIG. 2 shows PCR detection results of viruses extracted from honeybees after RNA extraction from collected honeybees according to an example of the present invention.

It can be confirmed from FIG. 2 and Table 7 that in the example, CBPV and BQCV were detected from samples 1, 2, 3, and 6; BQCV was detected from sample 4; and BQCV and SBV were detected from sample 5.

TABLE 8

|  | Sample 1 | Sample 2 | Sample 3 | Sample 4 | Sample 5 | Sample 6 |
|---|---|---|---|---|---|---|
| CBPV | W | W |  |  |  | W |
| BQCV | V | V | W | W | W | V |
| ABPV |  |  |  |  |  |  |
| KBV |  |  |  |  |  |  |
| SBV |  |  |  |  | V |  |
| DWV |  |  |  |  |  |  |
| IAPV |  |  |  |  |  |  |

Figure 3:
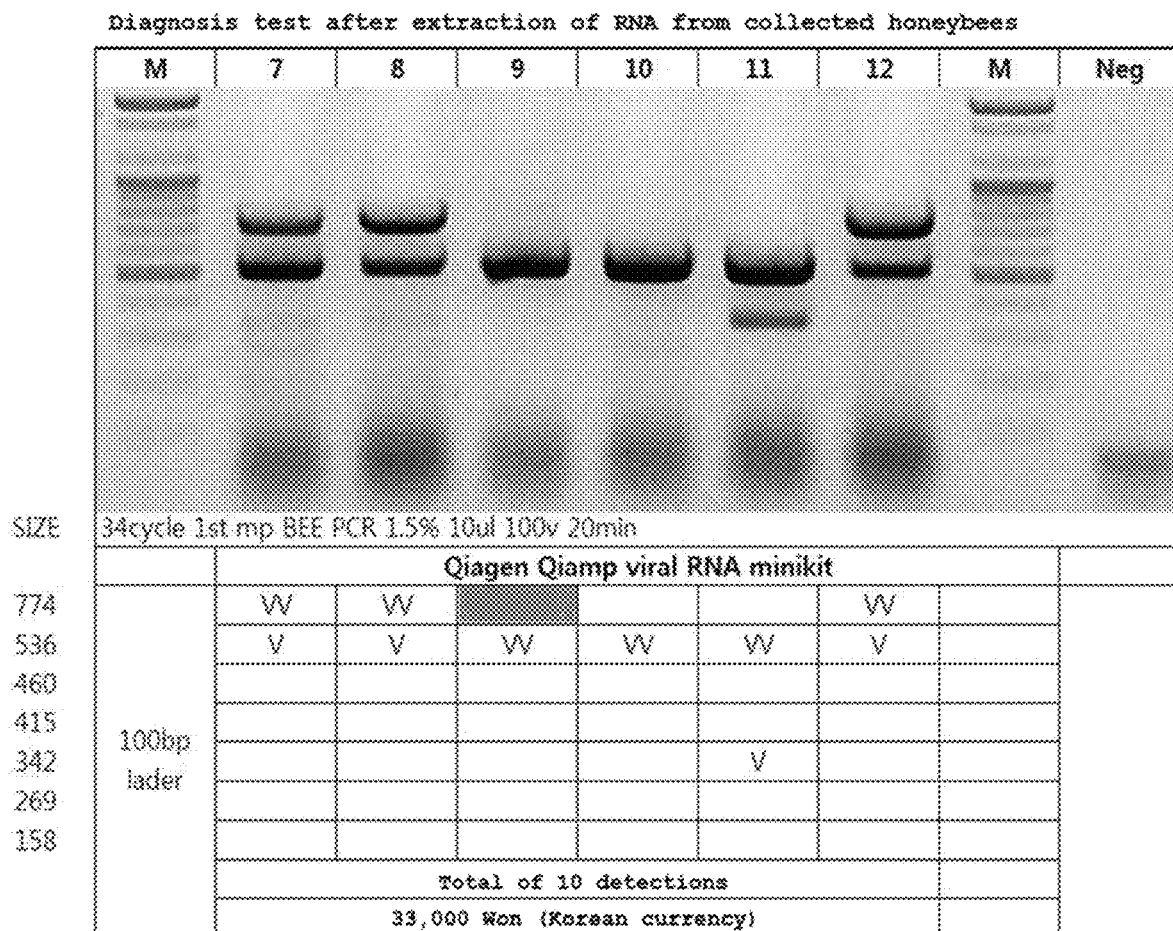
FIG. 3 shows PCR detection results of viruses extracted from honeybees after RNA extraction from collected honeybees according to an example of the present invention.

Meanwhile, it can be confirmed from FIG. 3 and Table 8 that in the control group (using QIAamp Viral RNA mini kit), CBPV and BQCV were detected from samples 1, 2, and 6; BQCV was detected from samples 3 and 4; and BQCV and SBV were detected from sample 5.

As for the control group (using QIAamp Viral RNA mini kit), CBPV was not detected from sample 3, but as for the example, CBPV was detected from sample 3.

Furthermore, the cost of extracting RNA and checking for the presence or absence of 7 species of viruses was about 33,000 won (Korean currency) for the control group, but about 3,000 won (Korean currency) for the example.

As a result of testing honeybees by using the composition for viral RNA extraction of the present invention, the present invention was 10 times cheaper and detected one more species of virus compared with the control group (using QIAamp Viral RNA mini kit) when the same samples were used.

INDUSTRIAL APPLICABILITY

The present invention relates to a composition for viral RNA extraction and a method for viral RNA extraction using the same.

This application contains references to amino acid sequences and/or nucleic acid sequences which have been submitted herewith as the sequence listing text file. The aforementioned sequence listing is hereby incorporated by reference in its entirety pursuant to 37 C. F. R. § 1.52(e).

What is claimed is:

1. A kit for viral RNA extraction from a sample, the kit comprising:
   (a) a homogenization solution containing, relative to a total amount thereof, 1-30 mM ethylenediaminetetraacetic acid (EDTA) and 0.1-2%(v/v) sodium chloride (NaCl);
   (b) a lysis buffer containing, relative to a total amount thereof, 0.1-1.5 M NaCl and 0.1-10%(v/v) sodium dodecyl sulfate (SDS); and
   (c) 1-6 M NaCl aqueous solution;
   (d) isopropanol;
   (e) silica membrane column;
   (f) a primary wash buffer containing, relative to a total amount thereof, 1-5 M sodium acetate; and
   (g) a secondary wash buffer containing 70-90% (v/v) ethanol aqueous solution,
   wherein none of the components comprise phenol or chloroform, and
   wherein none of the components comprise a chaotropic salt.

2. The kit of claim 1, wherein the sample is an individual being, a tissue, an organ, or cells of an animal.

3. The kit of claim 1, wherein the sample is seawater, tap water, bottled water, or water in a fish farm.

4. The kit of claim 2, wherein the animal is an arthropod.

5. The kit of claim 4, wherein the arthropod is an insect.

6. The kit of claim 1, wherein
   the homogenization solution consists of 1-30 mM ethylenediaminetetraacetic acid (EDTA) and 0.1-2%(v/v) sodium chloride (NaCl) relative to a total amount of the homogenization solution; and
   the lysis buffer consists of 0.1-1.5 M NaCl and 0.1-10% (v/v) sodium dodecyl sulfate (SDS) relative to a total amount of the lysis buffer.

7. A viral RNA extraction method, the method comprising:
   (a) a homogenizing step of homogenizing a sample by adding a homogenization solution containing, relative to a total amount thereof, 1-30 mM ethylenediaminetetraacetic acid (EDTA) and 0.1-2%(v/v) sodium chloride (NaCl);
   (b) a first centrifuging step of centrifuging the homogenized solution;
   (c) a first mixing step of mixing a lysis buffer with a first centrifugation supernatant and adding a 1-6 M NaCl aqueous solution, followed by mixing, wherein the lysis buffer contains, relative to a total amount thereof, 0.1-1.5 M NaCl and 0.1-10%(v/v) sodium dodecyl sulfate (SDS);
   (d) a second centrifuging step of centrifuging a lysis buffer mixture;
   (e) a second mixing step of mixing isopropanol with a second centrifugation supernatant;
   (f) a step of passing an isopropanol mixture through a silica membrane column;
   (g) a washing step of passing a wash buffer through the silica membrane column to wash the silica membrane column, wherein the wash buffer contains, relative to a total amount thereof, 1-5 M sodium acetate; and
   (h) an eluting step of eluting RNA from the silica membrane column wherein none of the components comprise phenol or chloroform, and wherein none of the components comprise a chaotropic salt.

8. The method of claim 7, wherein the washing step further comprises a step of washing the column with 70-90% (v/v) ethanol.

9. The method of claim 7, wherein the eluting step comprises a step of introducing a lysis buffer into the column to perform centrifugation.

10. The method of claim 7, wherein the sample is an individual being, a tissue, an organ, or cells of an animal.

11. The method of claim 7, wherein the sample is seawater, tap water, bottled water, or water in a fish farm.

12. The method of claim 10, wherein the animal is an arthropod.

\* \* \* \* \*

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: mpBEE-CBPV-F-774

<400> SEQUENCE: 1
aacctgcctc aacacaggca ac                                              22

<210> SEQ ID NO 2
<211> LENGTH: 23
<212> TYPE: DNA
<213> ORGANISM: Artificial Sequence
<220> FEATURE:
<223> OTHER INFORMATION: mpBEE-CBPV-R-774

<400> SEQUENCE: 2
acatctcttc ttcggtgtca gcc                                             23

<210> SEQ ID NO 3
<211> LENGTH: 23
<212> TYPE: DNA
<213> ORGANISM: Artificial Sequence
<220> FEATURE:
<223> OTHER INFORMATION: mpBEE-BQCV-F-536

<400> SEQUENCE: 3
ctttatcgag gaggagttcg agt                                             23

<210> SEQ ID NO 4
<211> LENGTH: 23
<212> TYPE: DNA
<213> ORGANISM: Artificial Sequence
<220> FEATURE:
<223> OTHER INFORMATION: mpBEE-BQCV-R-536

<400> SEQUENCE: 4
gcaatagata aagtgagccc tcc                                             23

<210> SEQ ID NO 5
<211> LENGTH: 22
<212> TYPE: DNA
<213> ORGANISM: Artificial Sequence
<220> FEATURE:
<223> OTHER INFORMATION: mpBEE-ABPV-F-460

<400> SEQUENCE: 5
```

```
ggtgccctat ttagggtgag ga                                           22

<210> SEQ ID NO 6
<211> LENGTH: 23
<212> TYPE: DNA
<213> ORGANISM: Artificial Sequence
<220> FEATURE:
<223> OTHER INFORMATION: mpBEE-ABPV-R-460

<400> SEQUENCE: 6
actacagaag gcaatgtcca aga                                          23

<210> SEQ ID NO 7
<211> LENGTH: 20
<212> TYPE: DNA
<213> ORGANISM: Artificial Sequence
<220> FEATURE:
<223> OTHER INFORMATION: mpBEE-KBV-F-415

<400> SEQUENCE: 7
gatgaacgtc gacctattga                                              20

<210> SEQ ID NO 8
<211> LENGTH: 19
<212> TYPE: DNA
<213> ORGANISM: Artificial Sequence
<220> FEATURE:
<223> OTHER INFORMATION: mpBEE-KBV-R-415

<400> SEQUENCE: 8
tgtgggtggc tatgagtca                                               19

<210> SEQ ID NO 9
<211> LENGTH: 23
<212> TYPE: DNA
<213> ORGANISM: Artificial Sequence
<220> FEATURE:
<223> OTHER INFORMATION: mpBEE-SBV-F-342

<400> SEQUENCE: 9
cgtaattgcg gagtggaaag att                                          23

<210> SEQ ID NO 10
<211> LENGTH: 24
<212> TYPE: DNA
<213> ORGANISM: Artificial Sequence
<220> FEATURE:
<223> OTHER INFORMATION: mpBEE-SBV-R-342

<400> SEQUENCE: 10
agattccttc gagggtacct catc                                         24

<210> SEQ ID NO 11
<211> LENGTH: 22
<212> TYPE: DNA
<213> ORGANISM: Artificial Sequence
<220> FEATURE:
<223> OTHER INFORMATION: mpBEE-DWV-F-269

<400> SEQUENCE: 11
tggtcaatta caagctactt gg                                           22

<210> SEQ ID NO 12
<211> LENGTH: 22
```

```
<212> TYPE: DNA
<213> ORGANISM: Artificial Sequence
<220> FEATURE:
<223> OTHER INFORMATION: mpBEE-DWV-R-269

<400> SEQUENCE: 12
tagttggacc agtagcactc at                                              22

<210> SEQ ID NO 13
<211> LENGTH: 22
<212> TYPE: DNA
<213> ORGANISM: Artificial Sequence
<220> FEATURE:
<223> OTHER INFORMATION: mpBEE-IAPV-F-158

<400> SEQUENCE: 13
ggtgccctat ttagggtgag ga                                              22

<210> SEQ ID NO 14
<211> LENGTH: 23
<212> TYPE: DNA
<213> ORGANISM: Artificial Sequence
<220> FEATURE:
<223> OTHER INFORMATION: mpBEE-IAPV-R-158

<400> SEQUENCE: 14
gggagtattg ctttcttgtt gtg                                             23
```